(12) United States Patent
Wada

(10) Patent No.: US 7,749,212 B2
(45) Date of Patent: Jul. 6, 2010

(54) DISPOSABLE WEARING ARTICLE AND METHOD OF MANUFACTURING THE SAME

(75) Inventor: Takao Wada, Settsu (JP)

(73) Assignee: Zuiko Corporation (JP)

(*) Notice: Subject to any disclaimer, the term of this patent is extended or adjusted under 35 U.S.C. 154(b) by 344 days.

(21) Appl. No.: 10/577,822

(22) PCT Filed: Nov. 4, 2004

(86) PCT No.: PCT/JP2004/016310

§ 371 (c)(1),
(2), (4) Date: Apr. 28, 2006

(87) PCT Pub. No.: WO2005/044168

PCT Pub. Date: May 19, 2005

(65) Prior Publication Data

US 2007/0038198 A1    Feb. 15, 2007

(30) Foreign Application Priority Data

Nov. 6, 2003    (JP) .............................. 2003-377267

(51) Int. Cl.
*A61F 13/15* (2006.01)
(52) U.S. Cl. ............... 604/385.29; 604/389; 604/385.3; 604/385.21; 604/385.24; 604/385.22; 604/385.26
(58) Field of Classification Search ................ 604/389, 604/385.3, 385.21, 385.24, 385.29, 385.22, 604/385.26
See application file for complete search history.

(56) References Cited

U.S. PATENT DOCUMENTS 4,681,580 A * 7/1987 Reising et al. ........... 604/385.3

FOREIGN PATENT DOCUMENTS

| JP | 10-286279 | 10/1998 |
|----|-----------|---------|
| JP | 11-104181 | 4/1999 |
| JP | 2003-527152 | 9/2003 |
| JP | 2003-528649 | 9/2003 |
| JP | 2003-528650 | 9/2003 |
| JP | 2003-529400 | 10/2003 |
| WO | WO 01/13843 A1 | 3/2001 |
| WO | WO 01/13849 A1 | 3/2001 |
| WO | WO 01/13851 A1 | 3/2001 |
| WO | WO 01/13852 A1 | 3/2001 |

* cited by examiner

*Primary Examiner*—Jacqueline F. Stephens
(74) *Attorney, Agent, or Firm*—Gerald E. Hespos; Michael J. Porco

(57) ABSTRACT

A back region having extensibility in a waist direction and provided with stopper members at both ends in the waist direction, an abdominal region provided with flap portions at both ends in the waist direction, and an absorber that bridges between the back region and the abdominal region are provided. It is set in such a manner that a length of the back region in the waist direction when it is stretched is longer than a length of the abdominal region in the waist direction, and a length of the back region in the waist direction when no force is applied from the outside is almost equal to the length of the abdominal region in the waist direction or shorter than the length in the waist direction.

9 Claims, 11 Drawing Sheets

DISPOSABLE WEARING ARTICLE AND METHOD OF MANUFACTURING THE SAME

BACKGROUND OF THE INVENTION

1. Field of the Invention

The present invention relates to a disposal wearing article and a manufacturing method of the same.

2. Description of the Related Art

There have been used tape-type diapers provided with tape-shaped mechanical fasteners (stopper members) that are attached at the both ends of the back region of the absorber and stopped on the front surface of the abdominal region in an attachable/detachable manner (for example, see Patent Documents 1 through 5). An elastic member for waist is provided to the back region and an elastic member for legs is provided to the crotch region.

Patent Document 1: Japanese Unexamined Patent Publication No. 11-104181

Patent Document 2: Japanese Unexamined Patent Publication No. 2003-527152

Patent Document 3: Japanese Unexamined Patent Publication No. 2003-528649

Patent Document 4: Japanese Unexamined Patent Publication No. 2003-528650

Patent Document 5: Japanese Unexamined Patent Publication No. 2003-529400

SUMMARY OF THE INVENTION

Tape-type diapers in the related art, however, have a problem that the waist portion is less elastic and the fitting property is poor when it is put on the wearer.

Also, because these diapers have no grab portions in the absorber portion corresponding to the abdominal region, when one puts a diaper on the wearer, it takes a time to stop the mechanical fasteners at the both ends of the back region on the front surface of the abdominal region. This raises a problem that these diapers are not readily put on the wearer.

The invention was devised to solve the problems discussed above, and therefore has an object to provide a disposable wearing article that can be readily put on the wearer while achieving an excellent fitting property, and a method of manufacturing the same.

According to an aspect of the invention, a disposable wearing article includes: a back region having extensibility in a waist direction and provided with stopper members at both ends in the waist direction; an abdominal region provided with flap portions at both ends in the waist direction; and an absorber that bridges between the back region and the abdominal region.

A length of the back region in the waist direction when the back region is stretched is longer than a length of the abdominal region in the waist direction, and the length of the back region in the waist direction when no force is applied from an outside is almost equal to the length of the abdominal region in the waist direction or shorter than the length in the waist direction.

These and other objects, features, aspects, and advantages of the present invention will become more apparent from the following detailed description of the preferred embodiments/examples with reference to the accompanying drawings.

BRIEF DESCRIPTION OF THE DRAWINGS

FIG. 1 shows a disposable diaper manufactured according to a first fabrication sequence.

DETAILED DESCRIPTION OF THE PREFERRED EMBODIMENTS

Hereinafter, the best mode for carrying out the invention will be described in detail with reference to the drawings.

Figure 1A:
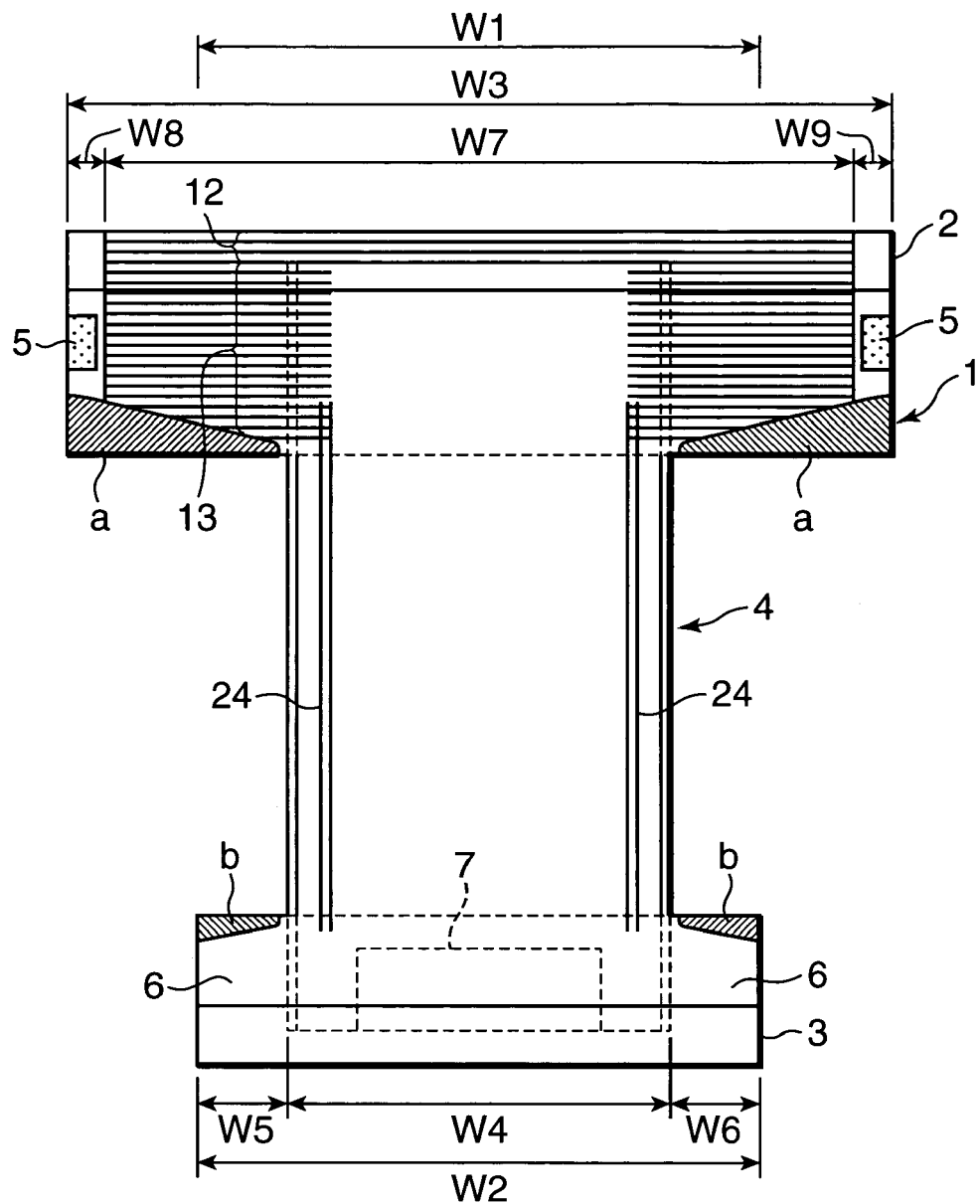
FIG. 1A is a developed plan view in a stretched state and FIG. 1B is a sectional front view of FIG. 1A.
Figure 1B:
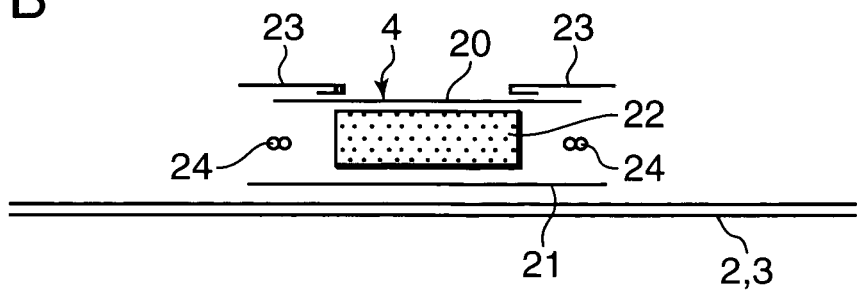
Figure 2:
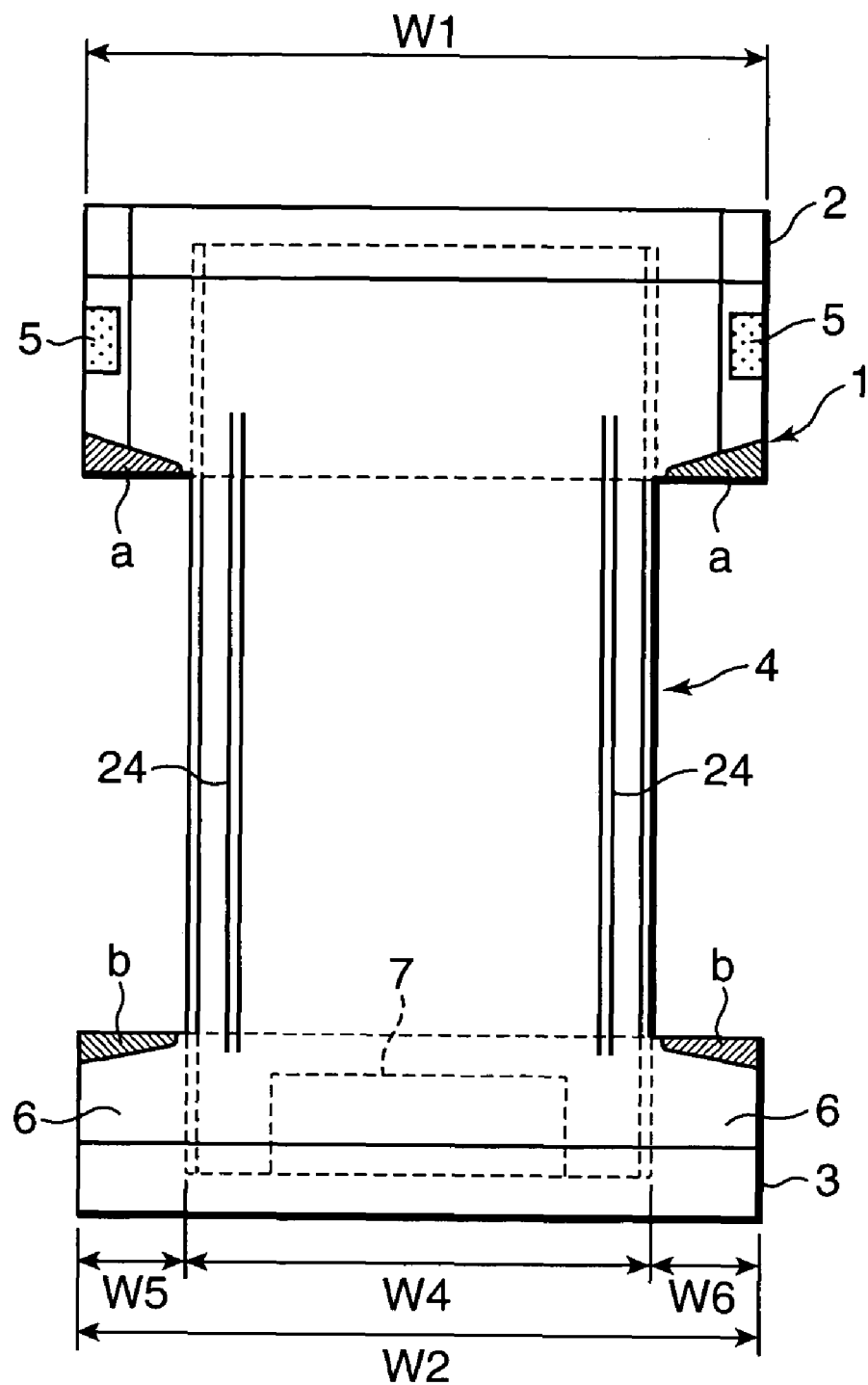
FIG. 2 is a developed plan view of the disposable diaper in a loosened state.
Figure 3:
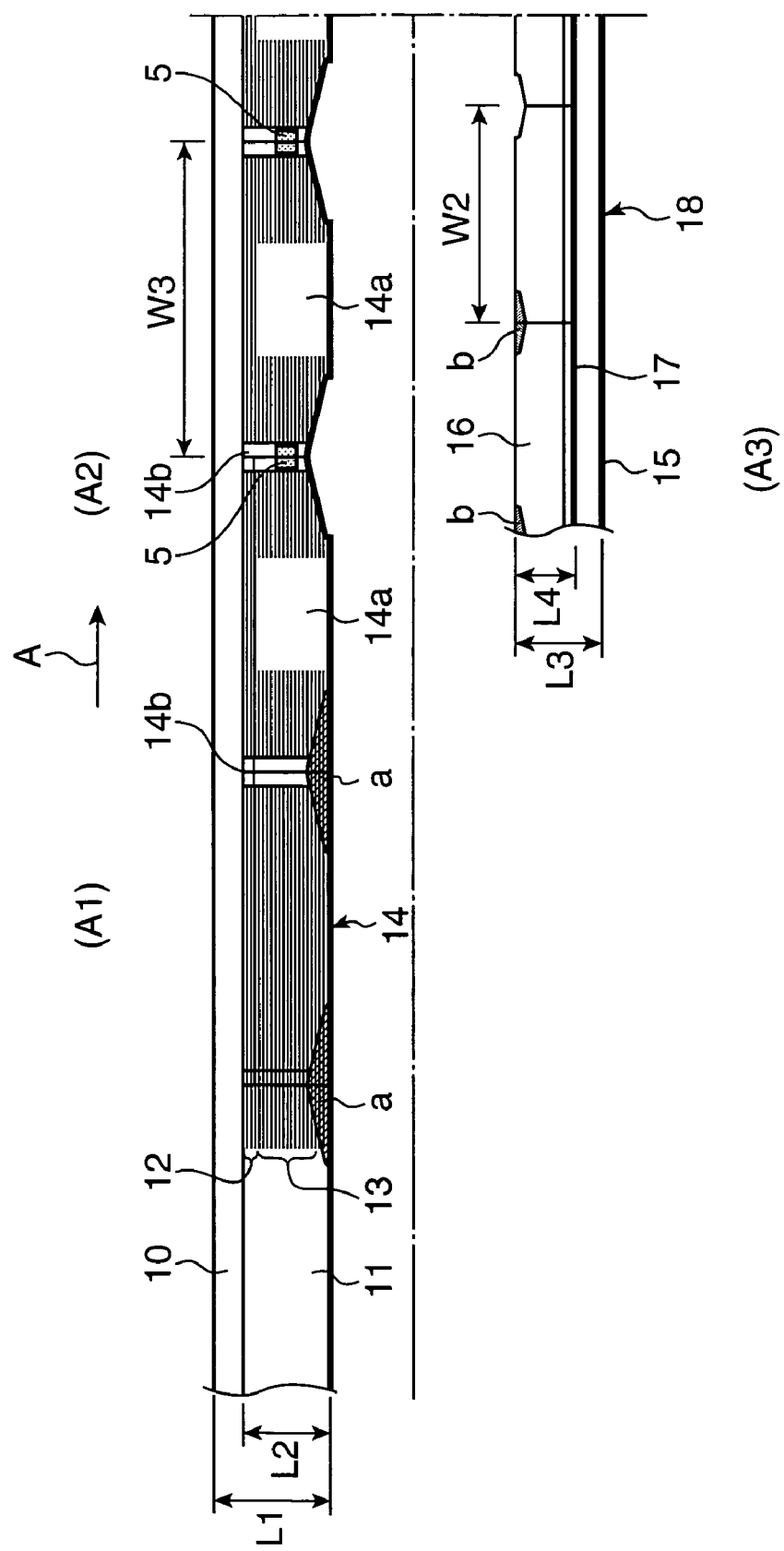
FIG. 3 is a view showing the first half of the first fabrication sequence of the disposable diaper.
Figure 4:
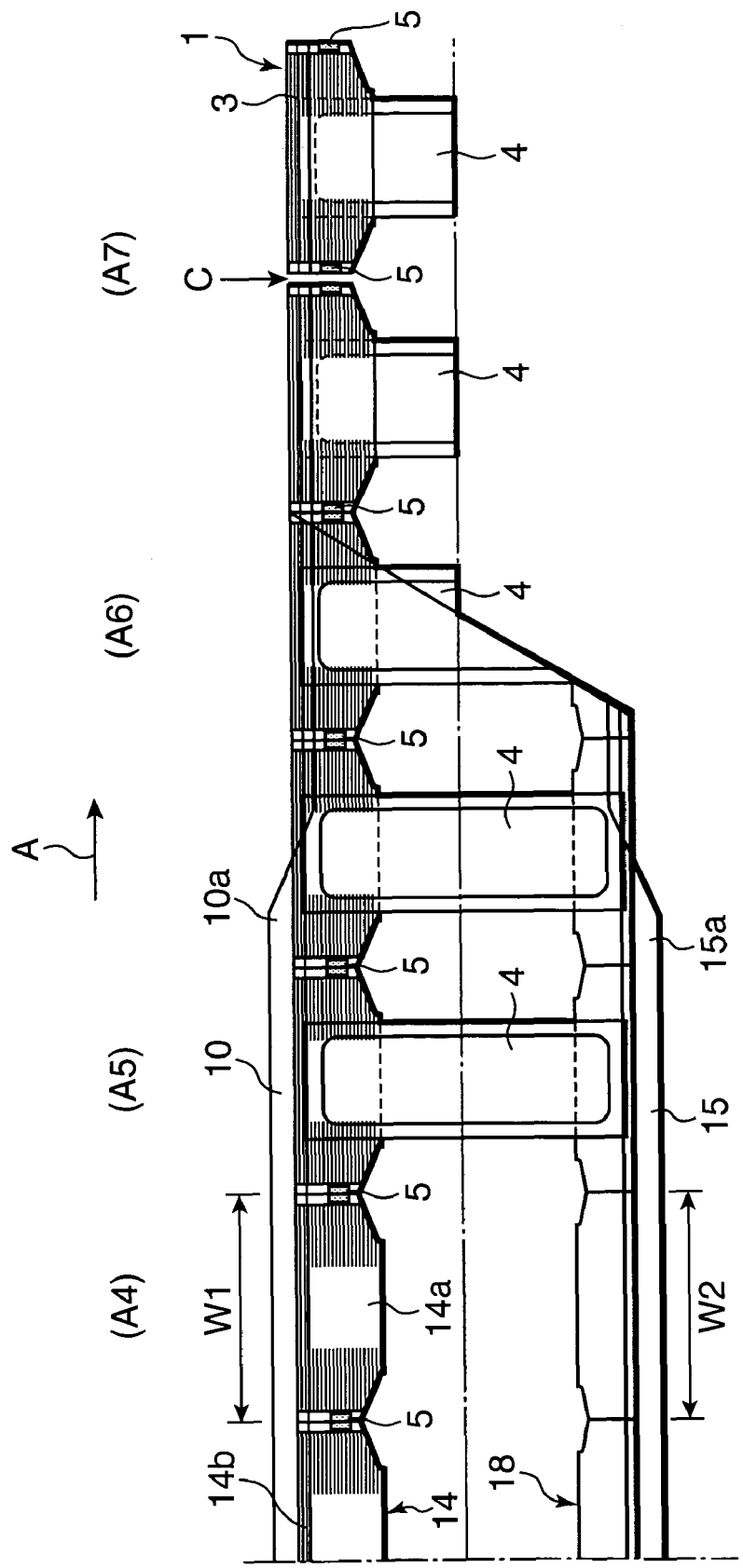
FIG. 4 is a view showing the second half of the first fabrication sequence of the disposable diaper.

FIG. 1 through FIG. 4 are views showing a disposable diaper (wearing article) 1 and a first fabrication sequence of the same. FIG. 1A is a developed plan view of the disposable diaper 1 in a stretched state. FIG. 1B is a sectional front view of FIG. 1A. FIG. 2 is a developed plan view of the disposable diaper 1 in a loosened state (when no force is applied from the outside). FIG. 3 is a view showing the fabrication sequence (first half) and FIG. 4 is a view showing the fabrication sequence (second half). FIG. 2 shows the disposable diaper 1 by omitting an elastic member in the back region.

Figure 11A:
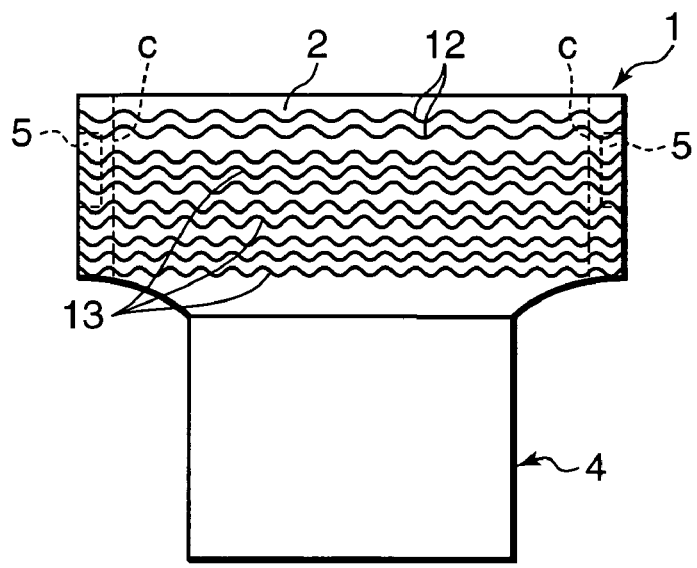
FIG. 11A is a rear view of the disposable diaper in a state finished as the product.
Figure 11B:
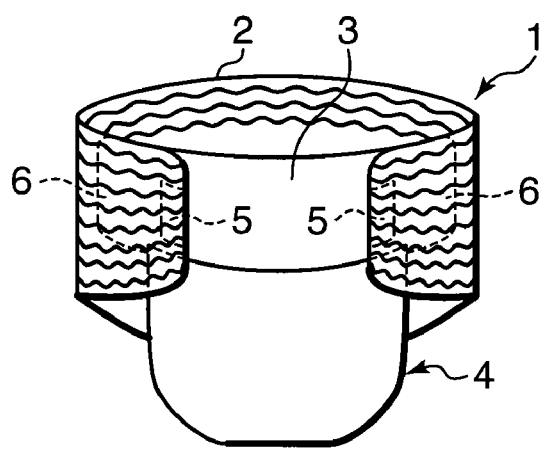
FIG. 11B is a perspective view of the disposable diaper in a wearing state.
Figure 11C:
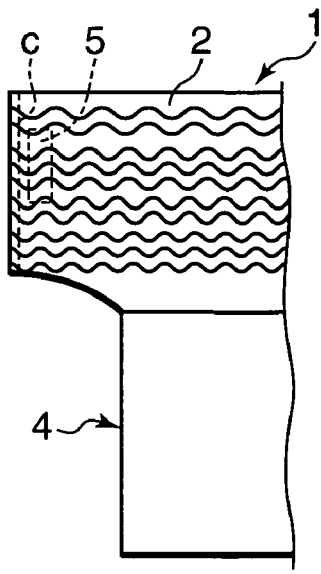
FIG. 11C is a rear view showing a major portion of the disposable diaper in the case of fusion joining.

FIG. 11A is a view showing an example of the disposable diaper 1 in a state finished as the product when viewed from the back region side. FIG. 11B is a perspective view showing an example of the disposable diaper 1 in a wearing state changed from the finished state when viewed from the abdominal region side. The disposable diaper 1 comprises a back region 2 having extensibility in a waist direction and provided with stopper members 5 at the both ends in the waist direction, an abdominal region 3 provided with flap portions (grab portions used during a stopping operation) 6 at the both ends in the waist direction, and an absorber 4 that bridges between the back region 2 and the abdominal region 3.

For the disposable diaper 1 shown in FIG. 1A, W3 is given as the length of the back region 2 in the waist direction in a stretched state, and W1 is given as the length in the waist direction in a state where no force is applied to the back region 2 from the outside (a state where the back region 2 is not stretched). In other words, with the disposable diaper 1, as is shown in FIG. 2, in a state where the back region 2 is not stretched, the length W1 of the back region 2 in the waist direction is almost equal to or shorter than a length W2 of the abdominal region 3 in the waist direction.

It is set in such a manner that a sum of a width (length in a direction orthogonal to the longitudinal direction) W4 of the absorber 4 on the abdominal region 3 side and a length W7 of the back region 2 in an extensible portion is the circumference length of the intended wearer in the waist direction. W4 is a length obtained by subtracting lengths W5 and W6 needed for the flap portions (grab portions) 6 from the length W2 of the abdominal region 3 in the waist direction [that is, W4=W2−(W5+W6)]. W7 is a length obtained by subtracting lengths W8 and W9 needed for stopper member attachment portions, joined portions, and so forth described below from the length W3 of the back region 2 in the waist direction in a stretched state [that is, (W7=W3−(W8+W9)].

It is preferable to set W7 to a length at which the back region will not be stretched to its full and leaves some ease when put on the wearer, because a feeling of tightness of the wearer can be avoided. The lengths W5 and W6 of the flap portions 6 depend on the intended wearer. For example, for a baby, it is preferable to set the W5 and W6 to about 50 to 60 mm because one can hold the disposable diaper 1 firmly when he/she puts it on the baby.

The first fabrication sequence when the disposable diaper 1 is manufactured in a transverse flow will now be described using FIG. 3 and FIG. 4. The right end of FIG. 3 showing the fabrication sequence (first half) continues to the left end of FIG. 4 showing the fabrication sequence (second half).

[Step A1] A first elastic member 12 for waist and a second elastic member 13 for body-fitting use are bonded to be sandwiched in a stretched state in a flow direction A between a first web 10 for outer surface on the lower side and a second web 11 for inner surface on the upper side that are continuously fed in the flow direction A. A first elastic laminated body 14 for the back region 2 is thus manufactured. It is preferable that the first web 10 and the second web 11 are made of non-woven fabric.

The elastic member can be a thread of natural rubber, a thread of synthetic rubber, a polyurethane-based elastic thread, a polyurethane-based elastic film, a polyolefin-based elastic film, a polystyrene-based elastic film, etc.

Regarding the bonding method, a hot melt bonding agent or the like may be applied to the first web 10, so that the second web 11 together with the first and second elastic members 12 and 13 is bonded thereto, or alternatively, a hot melt bonding agent or the like may be applied to the first and second elastic members 12 and 13, so that these members are bonded to the first and second webs 10 and 11. In the case of the latter method, the first and second elastic members 12 and 13 can be omitted when a bonding agent used per se has elasticity (for example, an elastic hot melt bonding agent). The same applies to the bonding in Step A2.

By taking a stretching ratio of each elastic member into account, each elastic member is set in such a manner that the length W1 of the back region 2 in the waist direction is almost equal to or shorter than the length W2 of the abdominal region 3 in the waist direction when a tensile force is adjusted in Step A4 described below.

Although the first and second elastic members 12 and 13 are illustrated in solid lines in FIG. 3 for easy understanding, because they are covered with the second web 11 on the upper side, to be accurate, they should be illustrated in a chained line. Some portions in FIG. 1, FIG. 2, and FIG. 4 are illustrated in the same manner.

[Step A2] Stopper members 5 are attached to the first elastic laminated boy 14 to be positioned at the both ends of the back region 2 in the waist direction. The stopper members 5 are referred to as a mechanical fastener or a Hook-and-Loop fastener. It comprises a pair of a hook portion and a loop portion, and when the hook portion and the loop portion are pressed hard against each other, they are stopped so that neither will readily come off from the other, while the hook portion and the loop portion are released from the stopping when the hook portion and the loop portion are peeled off hard by hand. The stopper members 5 form the hook portion. Regarding the loop portion making the pair, because non-woven fabric per se can function as the loop portion, the loop portion can be omitted by using non-woven fabric instead of providing the loop portion 7 (see a chained line of FIG. 1A). Alternatively, a bonding agent that can be peeled off repetitively may be used instead of the mechanical fastener.

[Step A3] A third elastic member 17 for waist is bonded to be sandwiched in a stretched state in the flow direction A between a third web 15 for outer surface on the lower side and a fourth web 16 for inner surface on the upper side that are fed continuously in the flow direction A. A second elastic laminated body 18 for abdominal region is thus manufactured. It is preferable that the third web 15 and the fourth web 16 are made of non-woven fabric.

Instead of the second elastic laminated body 18 for abdominal region, the third web 15 for outer surface alone, or a laminated body of the third web for outer surface and the fourth web for inner surface may be used as the member 18 for abdominal region.

[Step A4] Stretching of the first and second elastic members 12 and 13 is loosened by adjusting a tensile force of the first elastic laminated body 14 in the flow direction A for the length W1 of the back region 2 in the waist direction and the length W2 of the abdominal region 3 in the waist direction to become almost equal (W1≈W2).

More specifically, in the first elastic laminated body 14 up to Step A3, the first and second elastic members 12 and 13 are in a stretched state, and it is anticipated that the width W3 of the back region 2 in the waist direction at this point in time reaches the width W1 when loosened in Step A4. The back region 2 of the disposable diaper 1 shown in FIG. 1A is illustrated as the one having the length W3 in the waist direction, which is the length before it is loosened (stretched state). As is shown in FIG. 2, it has the length W1 in the waist direction which is almost equal to or shorter than the width W2 of the abdominal region 3 in the waist direction after it is loosened (in a state where no force is applied from the outside).

It is preferable that a tensile force is kept applied to the first elastic laminated body 14 to the extent that no sagging occurs after the stretching of the respective elastic members is loosened.

[Step A5] An absorber 4 is attached to bridge between the first elastic laminated body 14 and the second elastic laminated body 18 at the intermediate position of the two stopper members 5 attached to the back region 2, that is, at the intermediate position (attachment portion 14a descried below) between the back region 2 and the abdominal region 3 in the waist direction. As is shown in FIG. 1B, the absorber 4 comprises an absorbent core 22 disposed between a top sheet 20 and a back sheet 21. Cuffs (rising flaps) 23 may be provided at the both ends of the top sheet 20, and elastic members 24 for legs may be provided at the both ends of the absorbent core 22. These configurations are preferable because when the cuffs 23 are provided, it is possible to prevent leakage of body wastes, such as urine, from the leg portions, and when the elastic members 24 for legs are provided, the fitting property of the leg portions can be increased.

[Step A6] The first elastic laminated body 14 and the second elastic laminated body 18 are overlaid one on the other by folding the absorber 4. In this instance, the end 10a of the first web 10 of the first elastic laminated body 14 may be folded and bonded, and also the end 15a of the third web 15 of the second elastic laminated body 18 may be folded and bonded.

The step of folding the ends can be omitted by making the length L1 of the first web 10 for outer surface almost equal to the length L2 of the second web 11 for inner surface, and making the length L3 of the third web 15 for outer surface almost equal to the length L4 of the fourth web 16 for inner surface, all the lengths being in a direction orthogonal to the flow direction A.

[Step A7] The overlaid first elastic laminated body 14 and second elastic laminated body 18 are cut at an intermediate position C of the neighboring absorbers 4. In this instance, the stopper members 5 are also cut into the right and the left. The disposable diaper 1 is thus completed as the product.

Alternatively, the stopper members 5 may be attached to be positioned at the both ends of the cutting position C in Step A2, so that the cutting is performed at the intermediate position C of each stopper member 5 in Step A7.

The disposable diaper 1 manufactured according to the first fabrication sequence is formed in the shape of a capital T as is shown in FIG. 11A when viewed from the rear side (from the back region 2 side), and the stopper members (hook portions) 5 on the inner surface of the back region 2 are temporarily stopped on the inner surface of the abdominal region 3.

When one puts the disposal diaper 1 on the wearer, the abdominal region 3 and the back region 2 are pulled apart in the both directions and it is developed in the shape of a capital H as a tape-type diaper (see FIG. 1A). Then, the back region 2 is put on the bottom of the wearer, the absorber 4 is put on the crotch of the wearer, and the abdominal region 3 is put to the abdomen of the wearer. Subsequently, the both ends of the back region 2 are stretched in the waist direction to come around to the abdominal region 3 side, and by stopping the stopper members 5 at the both ends on the front surface (non-woven fabric used as the loop portion) of the abdominal region 3, the wearing state as shown in FIG. 11B is achieved.

With the disposable diaper 1 manufactured in this manner, the back region 2 has the extensibility in the waist direction, and when the back region 2 is stretched, it has the length W3 in the waist direction longer than the length W2 of the abdominal region 3 in the waist direction, and when the back region 2 is loosened (when it is not stretched), it has the length W1 in the waist direction almost equal to or shorter than W2. Hence, when one puts the disposable diaper 1 on the wearer, he stretches the back region 2 in the waist direction to come around to the abdominal region 3 side, and stops the stopper members 5 at the both ends on the front surface of the abdominal region 3. The extensibility in the waist direction therefore provides an excellent fitting property.

Also, because the flap portions (the grab portions used during a stopping operation) 6 (see FIG. 1A) are provided to the both ends of the abdominal region 3, when one puts the disposal diaper 1 on the wearer, he stretches the back region 2 and stops the stopper members 5 at the both ends on the front surface of the abdominal region 3 while holding the grab portions. This makes it easier to put the disposal diaper 1 on the wearer.

Further, according to the first fabrication sequence, the first elastic laminated body 14 for back region to which the first elastic member 12 for waist and the second elastic member 13 for body-fitting use have been bonded, and the second elastic laminated body 18 for abdominal region to which the third elastic member 17 for waist has been bonded are manufactured. Moreover, the stopper members 5 are attached to the first elastic laminated body 14, and the absorber 4 is attached to bridge between the first elastic laminated body 14 and the second elastic laminated body 18 while the stretching of the first and second elastic members 12 and 13 is loosened for the lengths W2 and W1 of the back region 2 and the abdominal region 3, respectively, in the waist direction to become almost equal. The first elastic laminated body 14 and the second elastic laminated body 18 are overlaid one on the other by folding the absorber 4, and by cutting the overlaid first elastic laminated body 14 and second elastic laminated body 18 at the intermediate position of the neighboring absorbers 4, disposable diapers 1 that can be readily put on the wearer while achieving an excellent fitting property can be manufactured continuously at a high speed.

Because the stopper members (hook portions) 5 on the inner surface of the back region 2 are temporarily stopped on the inner surface of the abdominal region 3, the disposable diaper 1 can be used directly as an underpants-type diaper without releasing the stopping of the stopper members 5 by pulling the abdominal portion 3 and the back region 2 hard in the both directions.

In this case, by adding a step of fusion joining (for example, by means of sheet sealing or sonic sealing) the first elastic laminated body 14 and the second elastic laminated body 18 at the inner portion of the stopper members 5 after Step A6, the peel strength is improved in comparison with a case where they are stopped by the stopper members 5 alone. The joined portions C (see FIG. 11A) can be peeled off when the abdominal region 3 and the back region 2 are pulled apart hard by hand in the both directions, and once they are peeled off, the both ends of the back region 2 can be stopped on the front surface of the abdominal region 3 by means of the stopper members 5. Also, as is shown in FIG. 1C, the stopper members 5 may be attached to the both ends of the back region 2 at the rather inner portions, so that the first elastic laminated body 14 and the second elastic laminated body 18 are fusion joined at the outside portion of the stopper members 5.

Alternatively, by eliminating Step A4 of attaching the stopper members 5 to the first elastic laminated body 14 to be positioned at the both ends of the back region 2, and by adding instead a step of fusion joining the first elastic laminated body 14 and the second elastic laminated body 18 after Step A6, it is possible to manufacture an underpants-type diaper.

The first elastic laminated body and the second elastic laminated body can be joined to each other by means of bonding using a hot melt bonding agent or the like instead of fusion joining.

It is preferable to add a step of applying processing to reduce a contraction force to the attachment portion 14a of the absorber 4 and to the attachment portions 14b of the stopper members 5 in the first elastic laminated body 14 between Step A1 and Step A2. In this case, the processing to reduce a contraction force is applied to the second elastic member 13 for body-fitting use alone in the attachment portion 14a of the absorber 4, and the processing to reduce a contraction force is applied to both the first elastic member 12 for waist and the second elastic member 13 for body-fitting use in the attachment portions 14b of the stopper members 5.

As the processing to reduce a contraction force, a method of fusing the first elastic member 12 and the second elastic member 13 using, for example, an embossed roll (heat embossing) (see JP-A-2002-113042), or a method of cutting the first elastic member 12 and the second elastic member 13 using a gather cutter can be adopted. The step of reducing a contraction force can be performed at any timing before Step A7 of attaching the absorber 4. By providing this Step, it is possible to prevent the occurrence of wrinkles in the absorber 4 and the stopper members 5.

It is preferable to add a step of cutting a trim a (see the hatched portion of FIG. 1) out of the first elastic laminated body 14 and cutting a trim b (see the hatched portion of FIG. 1) out of the second elastic laminated body 18 at any step before Step A6 of overlaying the first elastic laminated body 14 and the second elastic laminated body 18 one on the other. By adding this step, not only can the appearance of the disposable diaper 1 be enhanced, but also the fitting property to the legs can be satisfactory.

Figure 5:
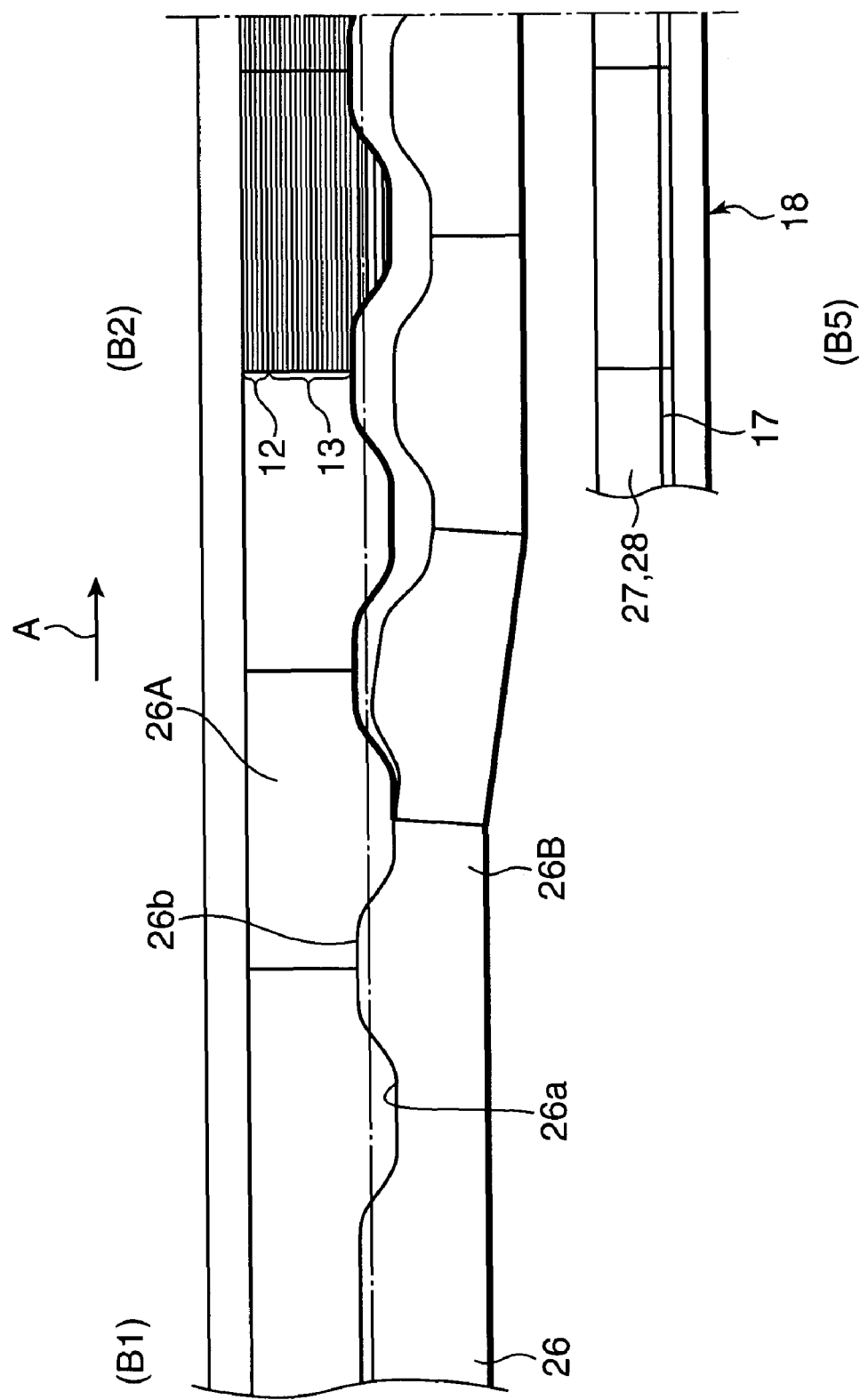
FIG. 5 is a view showing the first half of a second fabrication sequence of the disposable diaper.
Figure 6:
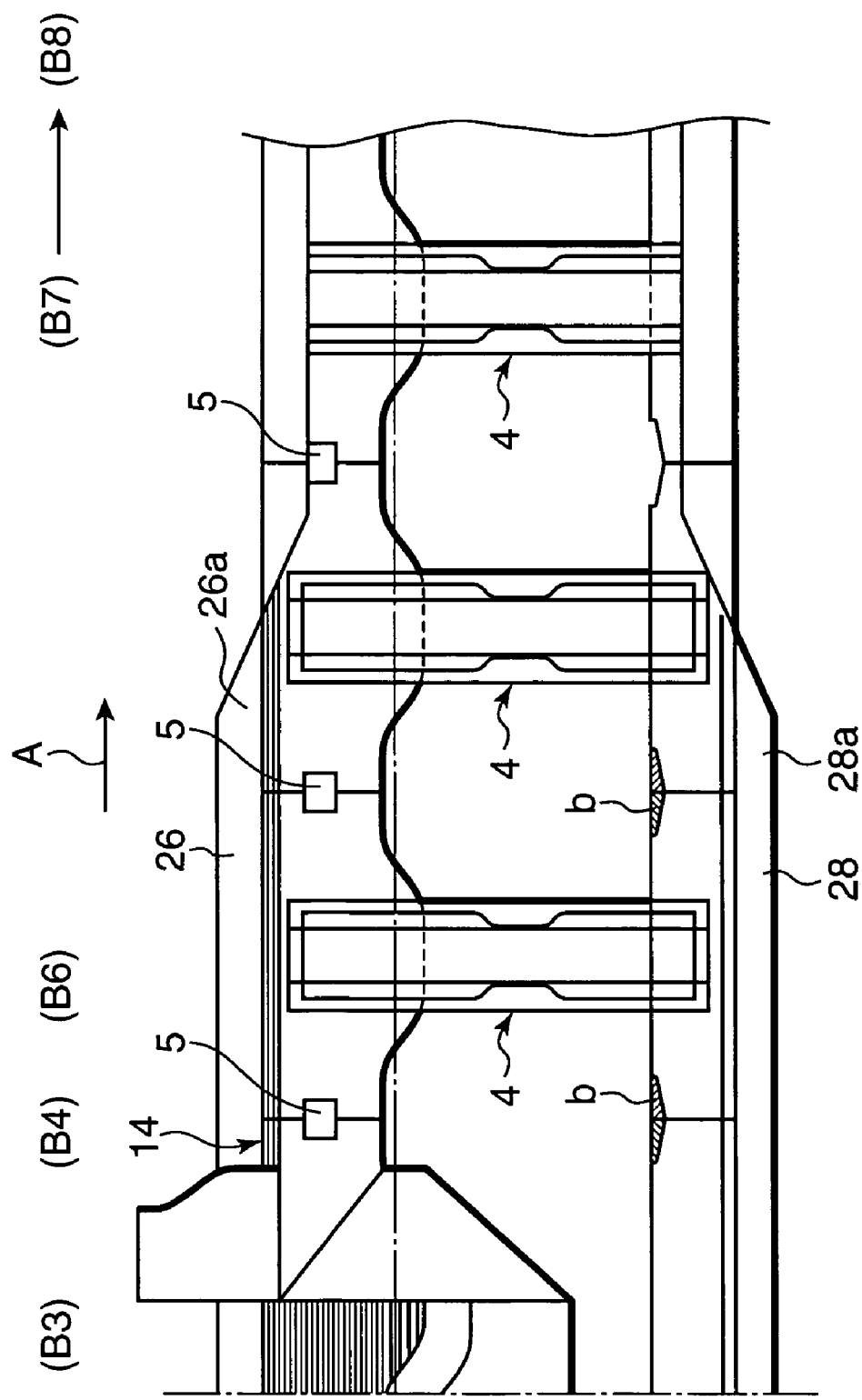
FIG. 6 is a view showing the second half of the second fabrication sequence of the disposable diaper.

FIG. 5 and FIG. 6 are views showing a second fabrication sequence of the disposable diaper (wearing article) 1. FIG. 5 is a view showing the fabrication sequence (first half) and FIG. 6 is a view showing the fabrication sequence (second half).

The second fabrication sequence to manufacture the disposable diaper 1 in a transverse flow will now be described using FIG. 5 and FIG. 6. The right end of FIG. 5 showing the fabrication sequence (first half) continues to the left end of FIG. 6 showing the fabrication sequence (second half). Also, because Steps B7 and B8 described below are the same as Steps A6 and A7 of the first fabrication sequence, illustrations of these steps are omitted herein.

[Step B1] A first web 26 that is fed continuously in a flow direction A is widened after it is cut along the flow direction in such a manner that a concave portion 26a and a convex portion 26b appear alternately (so-called S-cutting). An outer surface sheet 26A and an inner surface sheet 26B are thus manufactured.

[Step B2] Subsequently, the first elastic member 12 for waist and the second elastic member 13 for body-fitting use are bonded to the outer surface sheet 26A in a stretched state in the flow direction A.

[Step B3] The inner surface 26B sheet is then inverted so that the positions of the respective convex portions 26b of the outer surface sheet 26A and the inner surface sheet 26B coincide with each other, after which the inner surface sheet 26B is bonded to the outer surface sheet 26A on the surface to which the elastic members 12 and 13 have been bonded. The first elastic laminated body 14 for back region is thus manufactured.

[Step B4] The stopper members 5 are attached to the first elastic laminated body 14 to be positioned at the both ends of the back region 2.

[Step B5] A second elastic member 17 for waist is bonded to be sandwiched in a stretched state in the flow direction A between a second web 27 for outer surface on the lower side and a third web 28 for inner surface on the upper side that are fed continuously in the flow direction. The second elastic laminated body 18 for abdominal region is thus manufactured.

Instead of the elastic laminated body 18 for abdominal region, the third web 15 for outer surface alone, or a laminated body of the third web for outer surface and the fourth web for inner surface may be used as the member 18 for abdominal region.

[Step B6] After the stretching of the first and second elastic members 12 and 13 is loosened by adjusting the tensile force of the first elastic laminated body 14 in the flow direction A, the absorber 4 is attached to bridge between the first elastic laminated body 14 and the second elastic laminated body 18 at the intermediate position (the attachment portion 14a) of the back region 2 and the abdominal region 3 in the width direction.

[Step B7] The end 26a of the first web 26 of the first elastic laminated body 14 is folded and bonded, and the end 28a of the third web 28 of the second elastic laminated body 18 is folded and bonded. Then, the first elastic laminated body 14 and the second elastic laminated body 18 are overlaid one on the other by folding the absorber 4.

The step of folding the ends can be omitted as in [Step A6].

[Step B8] The overlaid first elastic laminated body 14 and second elastic laminated body 18 are cut at the intermediate position of the neighboring absorbers 4.

The disposable diaper 1 manufactured according to the second fabrication sequence can also achieve the same function and effect as the disposable diaper 1 manufactured according to the first fabrication sequence.

As in the first fabrication sequence, for the second fabrication sequence, it is also preferable to add a step of applying processing to reduce a contraction force to the attachment portion of the absorber 4 and to the attachment portions of the stopper members 5 in the first elastic laminated body 14 between Step B1 and Step B2.

As in the first fabrication sequence, it is preferable to add a step of fusion joining the first elastic laminated body 14 and the second elastic laminated body 18 at the inner portions of the stopper members 5 after Step B7.

Step B4 of attaching the stopper members 5 to the first elastic laminated body 14 to be positioned at the both ends of the back region 2 may be eliminated, and instead, a step of fusion joining the first elastic laminated body 14 and the second elastic laminated body 18 can be added after Step B7 as in the first fabrication sequence.

As in the first fabrication sequence, a step of cutting a trim b (see the hatched portion of FIG. 6) out of the second elastic laminated body 18 may be added after Step B5.

Different from the first fabrication sequence, because there is no need to cut a trim a (see the hatched portion of FIG. 1) out of the first elastic laminated body 14 in the second fabrication sequence, a trim loss can be lessened.

Figure 7:
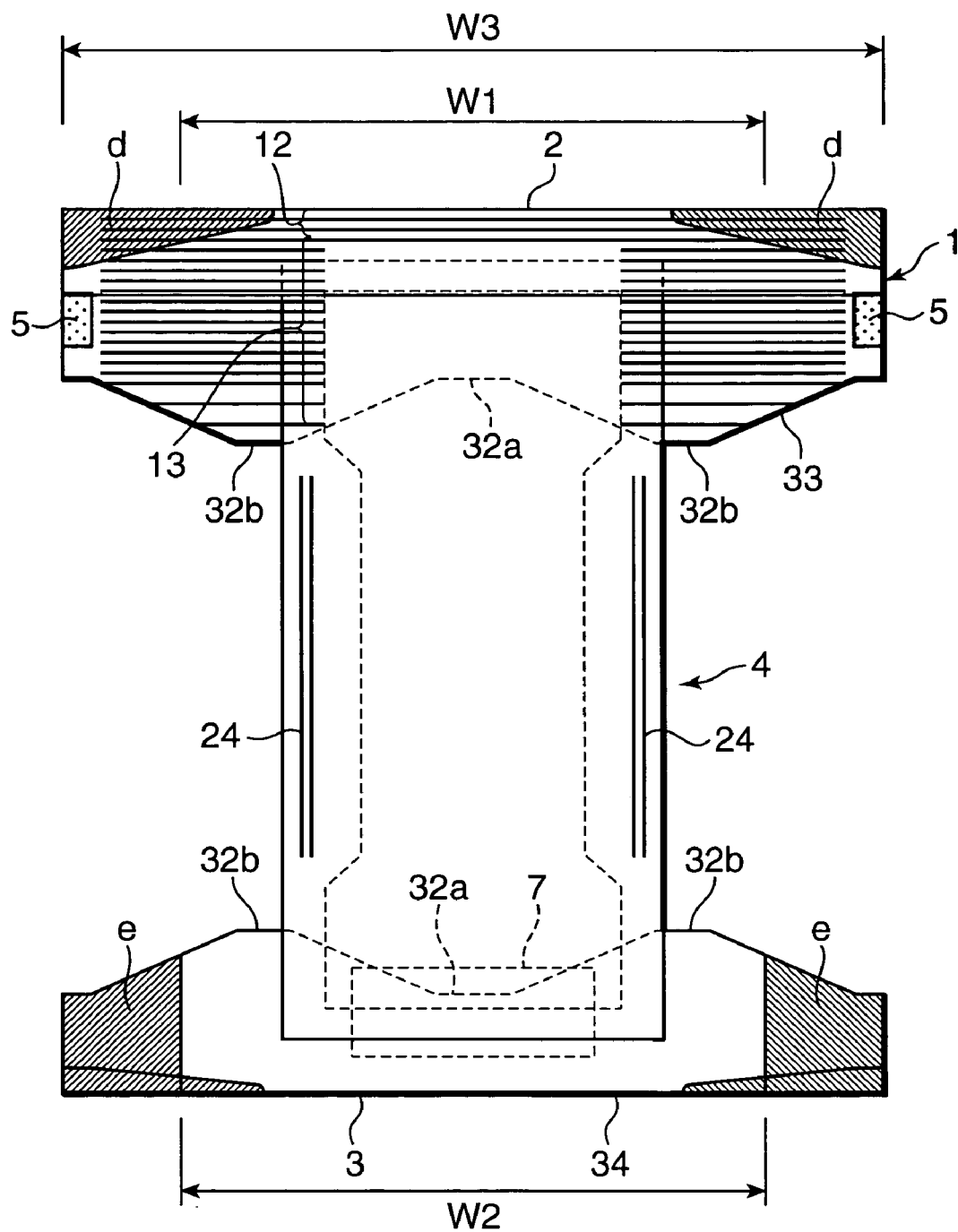
FIG. 7 is a developed plan view of a disposable diaper in a stretched state manufactured according to a third fabrication sequence.
Figure 8:
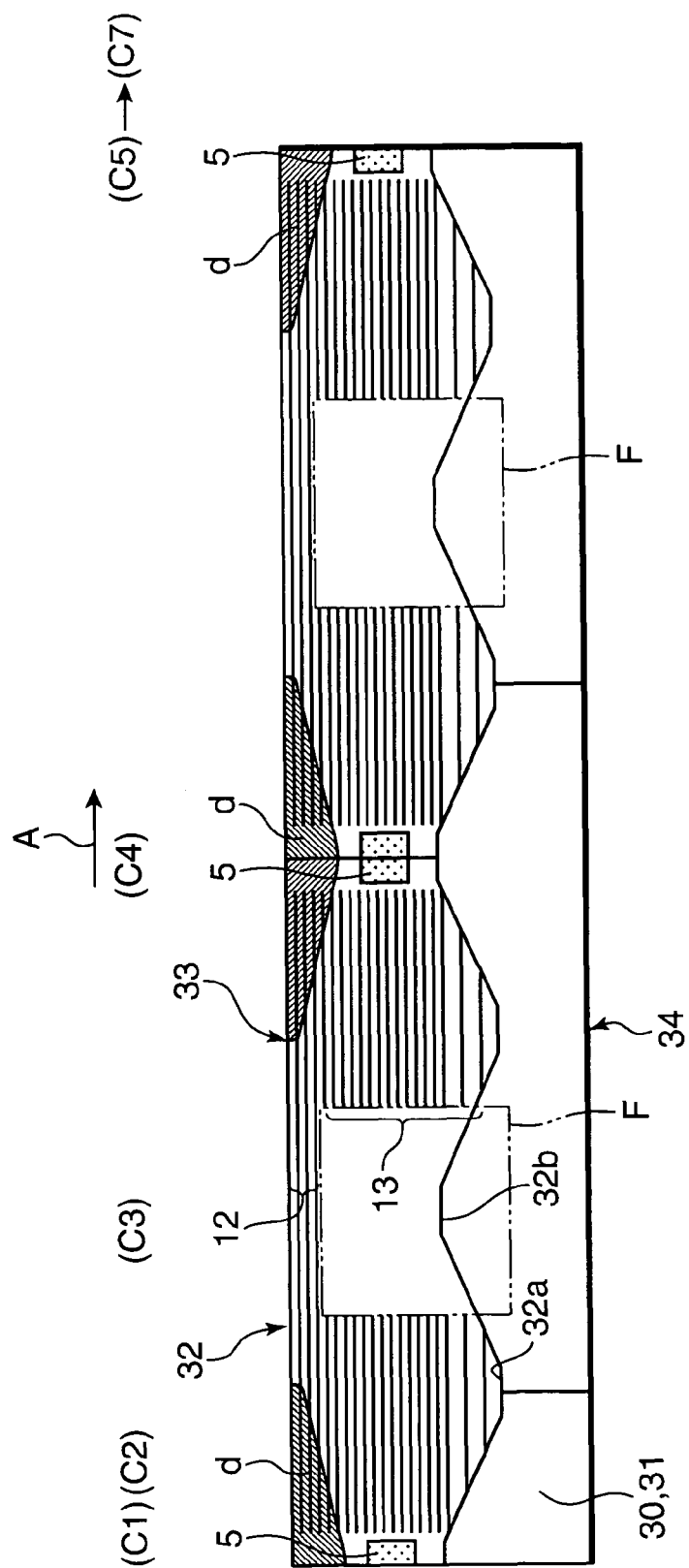
FIG. 8 is a view showing a major portion of the third fabrication sequence of the disposable diaper.

FIG. 7 and FIG. 8 are views showing a third fabrication sequence of the disposable diaper (wearing article) 1. FIG. 7 is a developed plan view of the disposable diaper 1 in a stretched state. FIG. 8 is a view showing a major portion of the fabrication sequence.

The third fabrication sequence to manufacture the disposable diaper 1 in a transverse flow will now be described briefly using FIG. 7 and FIG. 8.

[Step C1] The first elastic member 12 for waist (the first elastic member 12 on the abdominal region 3 side is omitted in FIG. 7 and FIG. 8. See FIGS. 9 and 10) and the second elastic member 13 for body-fitting use are bonded to be sandwiched in a stretched state in a flow direction between a first web 30 for outer surface on the lower side and a second web 31 for inner surface on the upper side that are fed continuously in a flow direction A, respectively, at the both ends of the two webs 30 and 31 in the width direction and at the portions other than the both ends of the two webs 30 and 31. A first elastic laminated body 32 is thus manufactured.

The first elastic laminated body 32 can be manufactured by omitting the first elastic member on the abdominal region 3 side.

[Step C2] The first elastic laminated body 32 is widened after it is cut along the flow direction A in such a manner that a concave portion 32a and a convex portion 32b appear alternately (so-called S-cutting). A second elastic laminated body 33 for back region including both the first elastic member 12 and the second elastic member 13, and a third elastic laminated body 34 for abdominal region including both the first elastic member 12 and the second elastic member 13 are thus manufactured.

[Step C3] A contraction force of the second elastic member 13 included in an absorber set portion 32a of the second elastic laminated body 33 (a frame F indicated by an alternate long and two short dashes line) is reduced. Alternatively, a contraction force of the second elastic member 13 included in an absorber set portion 32b of the third elastic laminated body 34 may be reduced.

[Step C4] The stopper members 5 are attached to the second elastic laminated body 33 to be positioned at the both ends of the back region.

[Step C5] The second elastic laminated body 33 and the third elastic laminated body 34 are shifted along the flow direction for the phases to be matched (see FIG. 7).

[Step C6] The absorber 4 is attached to bridge between the concave portion 32a of the second elastic laminated body 33 and the concave portion 32a of the third elastic laminated body 34 that oppose each other with their phases being matched (see FIG. 7).

[Step C7] A trim e is cut out of the third elastic laminated body 34, so that the abdominal region 3 has a length in the waist direction equal to the length W2 in the first fabrication sequence. The stretching of the first and second elastic members 12 and 13 is then loosened for the length W1 of the back region 2 in the waist direction and the length W2 of the abdominal region 3 in the waist direction to become almost equal (W1≈W2). Subsequently, the second elastic laminated body 33 is cut at the intermediate position of the neighboring absorbers 4 to have the length W3 in the waist direction, which is the length before it is loosened.

The second elastic laminated body 33 and the third elastic laminated body 34 are overlaid one on the other by folding the absorber 4. It should be noted, however, that these bodies are not necessarily overlaid.

The disposable diaper 1 manufactured according to the third fabrication sequence can also achieve the same function and effect as the disposable diaper 1 manufactured according to the first fabrication sequence.

In the third fabrication sequence, the absorber 4 may be attached to bridge between the respective concave portions 32b in Step C6.

Step C5 may be omitted, and instead, the absorber 4 may be attached to bridge between the concave portion 32a and the convex portion 32b in Step C6.

As is shown in FIG. 1C, it is possible to fusion join the second elastic laminated body 33 and the third elastic laminated body 34 at the outside portion of the stopper members 5 by attaching the stopper members 5 to the both ends of the back region 2 at rather inner portions.

Step C4 of attaching the stopper members 5 to the second elastic laminated body 33 to be positioned at the both ends of the back region 2 may be eliminated, and instead, a step of fusion joining the second elastic laminated body 33 and the third elastic laminated body 34 may be added after Step C7 as in the first fabrication sequence.

As in the first fabrication sequence, by adding a step of cutting a trim d out of the second elastic laminated body 33 at any step before Step C7 of overlaying the second elastic laminated body 33 and the third elastic laminated body 34 one on the other, not only can the appearance of the product be enhanced, but also the fitting property to the legs can be increased.

Figure 9:
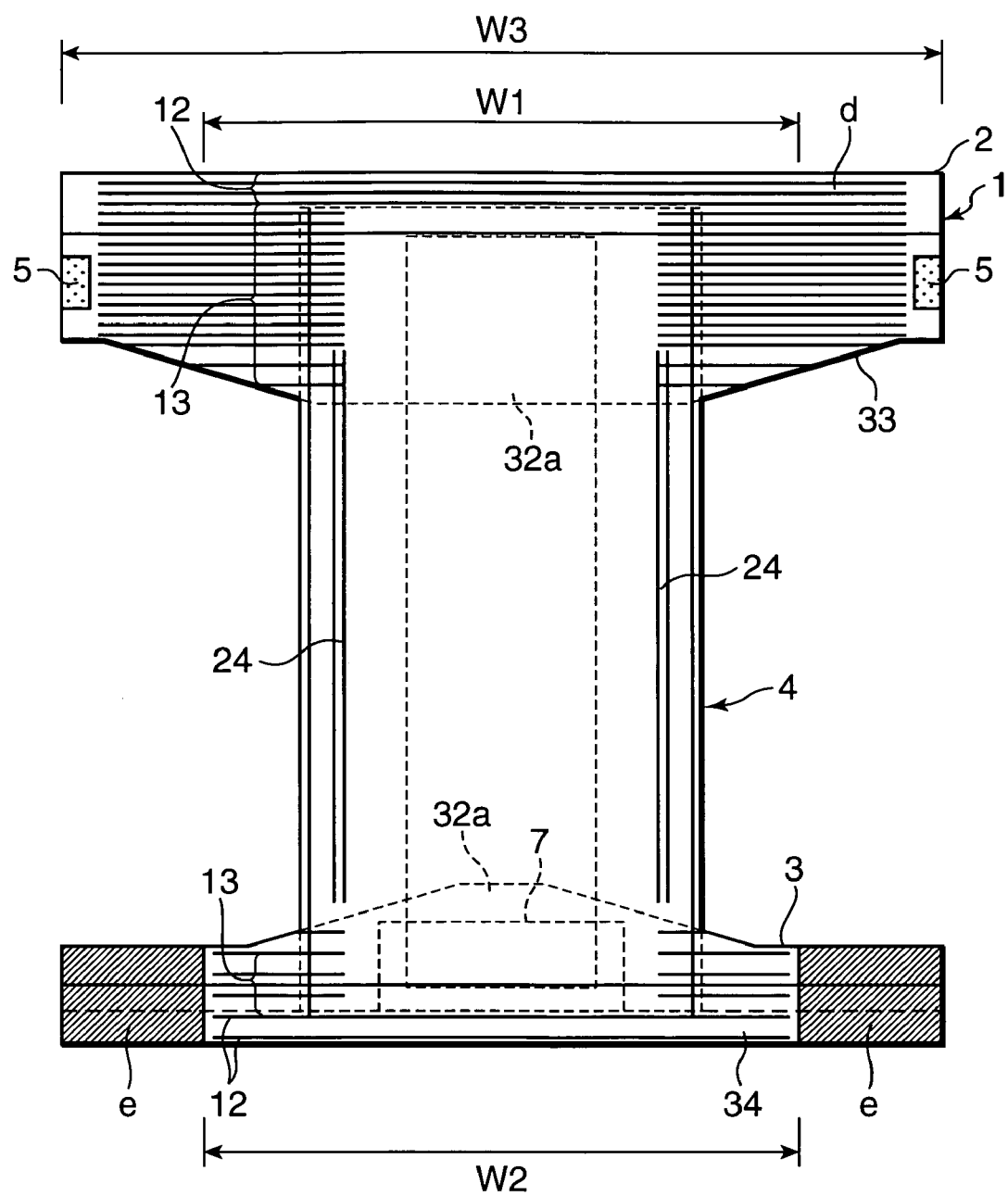
FIG. 9 is a developed plan view of a disposable diaper in a stretched state manufactured according to a modification of the third fabrication sequence.
Figure 10:
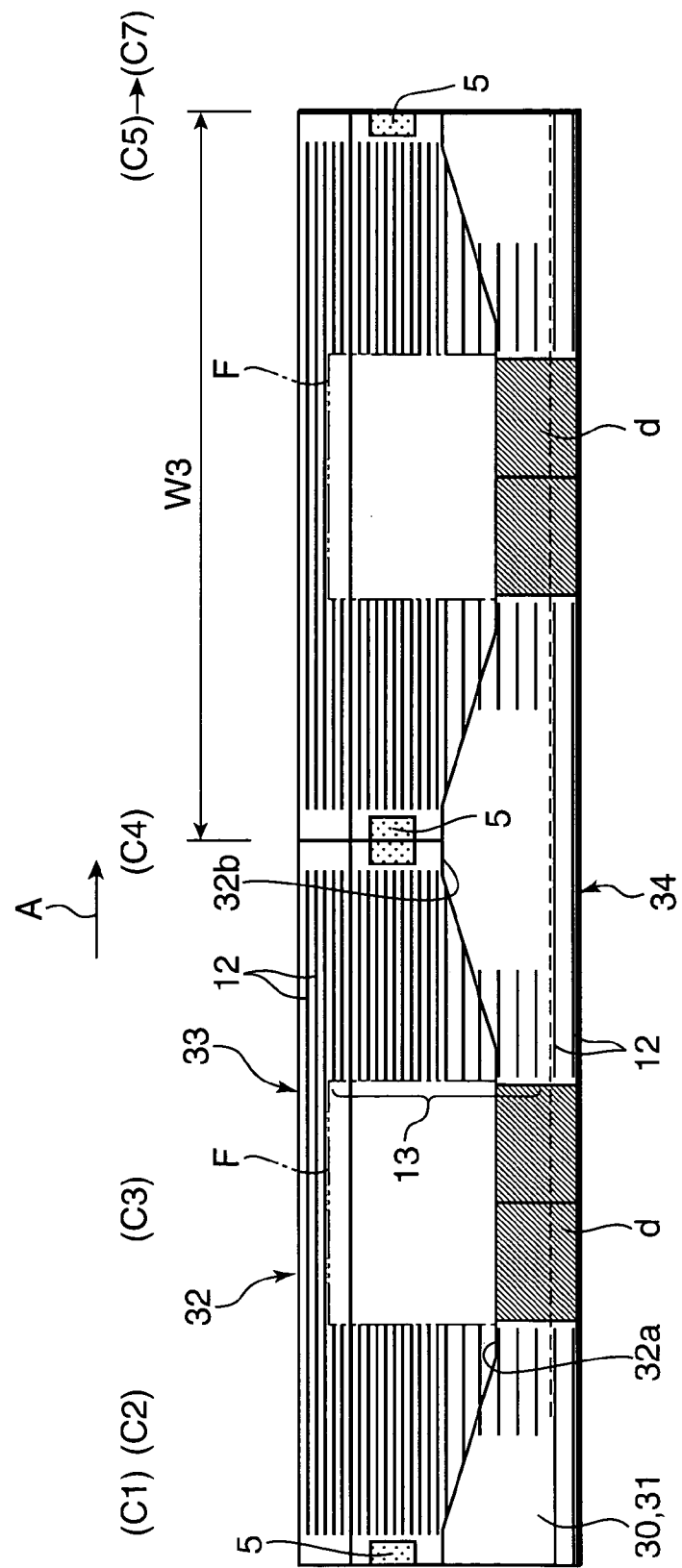
FIG. 10 is a view showing a major portion of the modification of the third fabrication sequence of the disposable diaper.

FIG. 9 and FIG. 10 show a modification of the third fabrication sequence of the disposable diaper (wearing article) 1. FIG. 9 is a developed plan view of the disposable diaper 1 in a stretched state. FIG. 10 is a view showing a major portion of the fabrication sequence.

A different point from the third fabrication sequence is that the second elastic laminated body 33 and the third elastic laminated body 34 are shifted along the flow direction in Step C5 for the respective convex portions 32a to oppose each other, and the absorber 4 is attached to bridge between the convex portion 32a of the second elastic laminated body 33 and the convex portion 32a of the third elastic laminated body 34 for every other opposing pair (see FIG. 9) in Step C6.

While the disposable diaper 1 has been described as an example of the disposable wearing article in the description above, the disposable wearing article of the invention is not limited to the example, and other examples include incontinence pants, sanitary briefs, and so forth.

As described above, a disposable wearing article comprises: a back region having extensibility in a waist direction and provided with stopper members at both ends in the waist direction; an abdominal region provided with flap portions at both ends in the waist direction; and an absorber that bridges between the back region and the abdominal region. A length of the back region in the waist direction when the back region is stretched is longer than a length of the abdominal region in the waist direction, and the length of the back region in the waist direction when no force is applied from an outside is almost equal to the length of the abdominal region in the waist direction or shorter than the length in the waist direction.

The back region has extensibility in the waist direction, and it is set in such a manner that the length of the back region in the waist direction when it is stretched is longer than the length of the abdominal region in the waist direction, and the length of the back region in the waist direction when no force is applied from the outside (when it is not stretched) is almost equal to the length of the abdominal region in the waist direction or shorter than the length of the abdominal region in the waist direction. The extensibility in the waist direction therefore provides an excellent fitting property.

Because the disposable wearing article is provided with the flap portions (grab portions used during a stopping operation) at the both ends of the abdominal region in the longitudinal direction (waist direction), when one puts the disposable wearing article on the wearer, he can stretch the back region to stop the stopper members at the both ends on the front surface of the abdominal region while holding the flap portions. This makes it easier to put the disposable wearing article on the wearer.

A disposable wearing article having a back region, an abdominal region, and an absorber that bridges between the back region and the abdominal region, is produced by: a step of manufacturing a first elastic laminated body for back region by bonding a first elastic member for waist and a second elastic member for body-fitting use to be sandwiched in a stretched state in a flow direction between a first web for outer surface and a second web for inner surface that are fed continuously in the flow direction; a step of attaching stopper members to the first elastic laminated body to be positioned at both ends of the back region in the waist direction; a step of manufacturing a second elastic laminated body for abdominal region by bonding a third elastic member for waist to be sandwiched in a stretched state in the flow direction between a third web for outer surface and a fourth web for inner surface that are fed continuously in the flow direction; a step of loosening stretching of the first and second elastic members by adjusting a tensile force of the first elastic laminated body in the flow direction for lengths of the back region and the abdominal region in the waist direction to become almost equal; a step of attaching the absorber to bridge between the first elastic laminated body and the second elastic laminated body at an intermediate position of the back region and the abdominal region in the waist direction; a step of overlying the first elastic laminated body and the second elastic laminated body one on the other by folding the absorber; and a step of cutting the overlaid first elastic laminated body and second elastic laminated body at an intermediate position of neighboring absorbers.

With this production method, the first elastic laminated body for back region to which the first elastic member for waist and the second elastic member for body-fitting use have been bonded and a second elastic laminated body for abdominal region to which the third elastic member for waist has been bonded are manufactured. Also, the stopper members are attached to the first elastic laminated body, and the absorber is attached to bridge between the first elastic laminated body and the second elastic laminated body while the stretching of the first and second elastic members is loosened for the widths of the back region and the abdominal region in the waist direction to become almost equal. The first elastic laminated body and the second elastic laminated body are overlaid one on the other by folding the absorber, and the overlaid first elastic laminated body and second elastic laminated body are cut at the intermediate position of the neighboring absorbers. In this manner, disposable wearing articles that can be readily put on the wearer while achieving an excellent fitting property can be manufactured continuously at a high speed.

A disposable wearing article having a back region, an abdominal region, and an absorber that bridges between the back region and the abdominal region, is produced by: a step of manufacturing an elastic laminated body for back region by bonding an elastic member to be sandwiched in a stretched state in a flow direction between a first web and a second web that are fed continuously in the flow direction; a step of attaching stopper members to the elastic laminated body to be positioned at both ends of the back region in a waist direction; a step of feeding a member for abdominal region continuously in the flow direction; a step of loosening stretching of the elastic member by adjusting a tensile force of the elastic laminated body in the flow direction for lengths of the back region and the abdominal region in the waist direction to become almost equal; a step of attaching the absorber to bridge between the elastic laminated body and the member for abdominal region at an intermediate position of two stopper members attached to the elastic laminated body; a step of overlying the elastic laminated body and the member for abdominal region one on the other by folding the absorber; and a step of cutting the overlaid elastic laminated body and member for abdominal region at an intermediate position of neighboring absorbers.

The elastic laminated body for back region to which the elastic member has been bonded is manufactured and the stopper members are attached to the elastic laminated body. While the elastic member is in a loosened state by adjusting a tensile force of the elastic laminated body for the lengths of the back region and the abdominal region in the waist direction to become almost equal, the absorber is attached to bridge between the elastic laminated body and the member for abdominal region at the intermediate position of the two stopper members. The elastic laminated body and the member for abdominal region are overlaid one on the other by folding the absorber, and the overlaid elastic laminated body and the member for abdominal region are cut at the intermediate position of the neighboring absorbers. In this manner, disposable wearing articles that can be readily put on the wearer while achieving an excellent fitting property can be manufactured continuously at a high speed.

A disposable wearing article that can be readily put on the wearer while achieving an excellent fitting property and the method of manufacturing the same are provided.

The invention claimed is:

1. A disposable wearing article comprising:
    a back region having extensibility in a waist direction, the back region defining a first length in the waist direction when the back region is in an unstretched condition and a second length in the waist direction when the back region is in a maximum stretched condition and stopper members being provided at both ends of the back region in the waist direction;
    an abdominal region independent of and spaced apart from the back region, the abdominal region being provided with flap portions at both ends in the waist direction; and
    an absorber that bridges between and connects the spaced apart back region and the abdominal region,
    wherein the second length of the back region in the waist direction is longer than a maximum length of the abdominal region that can be achieved in the waist direction, and the first length of the back region in the waist direction when no force is applied to the back region from an outside is almost equal to the length of the abdominal region in the waist direction or shorter than the length of the abdominal region in the waist direction when no force is applied to the abdominal region from the outside.

2. The disposable wearing article according to claim 1, wherein the back region includes a web for outer surface, a web for inner surface, and an elastic member provided between the web for outer surface and the web for inner surface, the elastic member is extendable in the waist direction.

3. The disposable wearing article according to claim 1, wherein a trimmed portion is provided on an inner edge of each of the both ends of the back region, and on an inner edge of the flap portions.

4. The disposable wearing article according to claim 1, wherein a slanting portion is provided on an inner edge of each of the both ends of the back region, and on an inner edge of each of the flap portions.

5. The disposable wearing article according to claim 1, wherein the stopper members are temporarily held on the abdominal region to form the disposable wearing article into an underpants-shape, and the back region and the abdominal region are joined at an inside from the stopper member.

6. The disposable wearing article according to claim 1, wherein the stopper members are temporarily held on the abdominal region to form the disposable wearing article into an underpants-shape, and the back region and the abdominal region are joined at an outside from the stopper member.

7. The disposable wearing article according to claim 1, wherein a length of each of the flap portions is 50 to 60 mm.

8. The disposable wearing article according to claim 1, wherein the abdominal region has substantially no extensibility in the waist direction.

9. The disposable wearing article according to claim 1, wherein
    the stopper members are provided at an inner position with respect to the both ends of the back region in the waist direction, and
    the back region has the extensibility over the entirety of the both ends of the back region.

* * * * *